United States Patent

Tirpak et al.

Patent Number: 5,296,160
Date of Patent: Mar. 22, 1994

[54] AQUEOUS DISPERSIONS OF BLOCKED POLYISOCYANATES

[75] Inventors: Robin E. Tirpak, Wheeling; James W. Rosthauser, Glendale, both of W. Va.

[73] Assignee: Miles Inc., Pittsburgh, Pa.

[21] Appl. No.: 734,708

[22] Filed: Jul. 23, 1991

[51] Int. Cl.⁵ .............................................. C09K 3/00
[52] U.S. Cl. ................................................ 252/182.2
[58] Field of Search ............ 252/182.2, 182.21, 182.22; 560/26

[56] References Cited

U.S. PATENT DOCUMENTS

| | | | |
|---|---|---|---|
| 3,933,677 | 1/1976 | Aufdermarsh | 252/188.3 R |
| 3,997,592 | 12/1976 | Aufdermarsh | 560/26 |
| 4,098,933 | 7/1978 | Burkhardt et al. | 427/379 |
| 4,119,602 | 10/1978 | Isgur et al. | 528/45 |
| 4,246,132 | 1/1981 | Gras et al. | 252/182.2 |
| 4,284,544 | 8/1981 | Wegner et al. | 260/29.2 |
| 4,357,441 | 11/1982 | Hamamura et al. | 524/591 |
| 4,522,851 | 6/1985 | Rosthauser | 427/386 |
| 4,596,744 | 6/1986 | Anderson et al. | 528/45 |
| 4,663,377 | 5/1987 | Hombach et al. | 524/196 |
| 4,824,925 | 4/1989 | Kamarchik et al. | 528/45 |
| 4,888,124 | 12/1989 | Blum et al. | 252/182.2 |
| 4,904,522 | 2/1990 | Markusch | 428/288 |

FOREIGN PATENT DOCUMENTS

| | | |
|---|---|---|
| 424697 | 5/1991 | European Pat. Off. . |
| 3807555 | 9/1988 | Fed. Rep. of Germany . |

*Primary Examiner*—Edward A. Miller
*Attorney, Agent, or Firm*—Joseph C. Gil; Thomas W. Roy

[57] ABSTRACT

The present invention is directed to a process for the preparation of an aqueous dispersion of a blocked polyisocyanate by reacting an aqueously dispersed polyisocyanate having an isocyanate content of at least 12% by weight, based on the weight of the polyisocyanate, with a monofunctional blocking agent which is more reactive with isocyanate groups than water at an equivalent ratio of monofunctional blocking groups to isocyanate groups of 0.5:1 to 2:1. The present invention is also directed to the aqueously dispersed blocked polyisocyanates prepared by this process and to compositions containing these polyisocyanates and an isocyanate-reactive compound.

8 Claims, No Drawings

AQUEOUS DISPERSIONS OF BLOCKED POLYISOCYANATES

BACKGROUND OF THE INVENTION

1. Field of the Invention

The present invention is directed to a process for the preparation of aqueous dispersions of blocked polyisocyanates, to the blocked polyisocyanate prepared by this process and to their use in aqueous dispersions which additionally contain an isocyanate-reactive component.

2. Description of the Prior Art

U.S. Pat. No. 4,904,522 is directed to the preparation of water dispersible polyisocyanates for use in fiberglass binder applications. In addition, U.S. Pat. No. 4,663,377 is directed to the use of water dispersible polyisocyanates in adhesive applications.

The disadvantage of these products is that after they are dispersed in aqueous media, they begin to react with water, which means these products have a limited potlife. Waiting too long to apply the product usually results in precipitation and/or formation of insoluble, non-film forming ureas. Even when these products are applied directly after the aqueous dispersions are formed, there is a problem. If film formation occurs before the water/isocyanate reaction is complete, subsequent carbon dioxide formation will result in bubbles in the film rendering it useless for coatings applications.

One solution to the problems of limited potlife and bubble formation is to block the isocyanate groups of the water dispersible polyisocyanate prior to dispersing it in water as described in U.S. Pat. Nos. 4,522,851, 4,098,933 and 4,284,544. The disadvantage of blocking the polyisocyanate before it is dispersed in water is that the blocked polyisocyanate is generally a solid or a high viscosity liquid which is very difficult or impossible to disperse in water without first diluting the blocked polyisocyanate in an organic solvent or heating the blocked polyisocyanate to an elevated temperature to reduce its viscosity.

Because one of the primary reasons for dispersing polyurethanes and polyisocyanates in water is to avoid the unnecessary use of organic solvents, it is certainly not desirable to have to dilute the blocked polyisocyanate with an organic solvent in order to reduce its viscosity sufficiently to disperse it in water. In addition, the extra energy costs and time which are necessary to heat the blocked polyisocyanate to an elevated temperature to reduce its viscosity are also undesirable.

Accordingly, an object of the present invention is to provide a process for preparing a blocked polyisocyanate which does not require substantial amounts of solvent or elevated temperatures in order to disperse the polyisocyanate in water.

Surprisingly, this object may be achieved in accordance with the present invention as described hereinafter.

SUMMARY OF THE INVENTION

The present invention is directed to a process for the preparation of an aqueous dispersion of a blocked polyisocyanate by reacting an aqueously dispersed polyisocyanate having an isocyanate content of at least 12% by weight, based on the weight of the polyisocyanate, with a monofunctional blocking agent which is more reactive with isocyanate groups than water at an equivalent ratio of monofunctional blocking groups to isocyanate groups of 0.5:1 to 2:1.

The present invention is also directed to the aqueously dispersed blocked polyisocyanates prepared by this process and to compositions containing these polyisocyanates and an isocyanate-reactive compound.

DETAILED DESCRIPTION OF THE INVENTION

Suitable polyisocyanates for use in preparing the polyisocyanates to be dispersed in water in accordance with the present invention include the known aliphatic, cycloaliphatic, araliphatic, aromatic and heterocyclic polyisocyanates. Suitable examples of these polyisocyanates include those described by W. Siefken in Justus Liebigs Annalen der Chemie, 562, pages 75 to 136. Prior to being dispersed in water, the polyisocyanates have an isocyanate content of at least about 12%, preferably at least about 15% and more preferably at least about 20% by weight, based on the weight of the polyisocyanate. Polyisocyanates having a lower isocyanate content and prepared, e.g., by reacting a monomeric polyisocyanate with a high molecular weight polyol, have sufficiently high viscosities that it is difficult to disperse them in water even if they are hydrophilically modified.

Examples of suitable monomeric polyisocyanates include 1,6-hexamethylene diisocyanate, 1,12-dodecane diisocyanate, cyclobutane-1,3-diisocyanate, cyclohexane-1,3- and/or -1,4-diisocyanate, 1-isocyanato-3,3,5-trimethyl-5-isocyanatomethyl cyclohexane (isophorone diisocyanate), 2,4-and/or 2,6-hexahydrotoluylene diisocyanate, hexahydro-1,3- and/or -1,4-phenylene diisocyanate, perhydro-2,4'- and/or -4,4'-diphenylmethane diisocyanate, 1,3- and/or 1,4-phenylene diisocyanate, 2,4- and/or 2,6-toluylene diisocyanate, diphenylmethane-2,4'- and/or -4,4'-diisocyanate, napthalene-1,5-diisocyanate, triphenylmethane-4,4',4''-triisocyanate and polyphenyl polymethylene polyisocyanates obtained by phosgenating aniline/formaldehyde condensation products. Also suitable are polyisocyanates adducts containing urea, biuret, urethane, allophanate, uretdione or carbodiimide groups or isocyanurate rings. These adducts may be prepared from any known monomeric polyisocyanates, especially those set forth above, by known methods. When using low molecular weight, highly volatile diisocyanates, it is especially preferred to convert these diisocyanates into adducts with lower monomeric diisocyanate contents prior to dispersing them in water. It is also possible to use mixtures of any of these monomeric polyisocyanates and/or polyisocyanate adducts.

In general, it is particularly preferred to use readily available polyisocyanates such as polyphenyl polymethylene polyisocyanates ("crude MDI") and polyisocyanate adducts containing carbodiimide groups, urethane groups, allophanate groups, isocyanurate groups, uretdione groups or biuret groups, especially those based on 2,4- and/or 2,6-toluylene diisocyanate ("TDI"), 1,6-hexamethylene diisocyanate, isophorone diisocyanate and mixtures thereof.

The polyisocyanates or polyisocyanate adducts used to prepare the aqueous dispersions of the present invention may be used in their unmodified, hydrophobic form or preferably they may be rendered hydrophilic by admixture with external emulsifiers or by reaction with cationic, anionic and/or nonionic compounds containing isocyanate-reactive groups. The reaction components which ensure the dispersibility of the polyisocyanates include compounds containing lateral or terminal, hydrophilic ethylene oxide units and compounds containing ionic groups or potential ionic groups.

The compounds containing lateral or terminal, hydrophilic ethylene oxide units contain at least one, preferably one, isocyanate-reactive group and are used in an amount sufficient to provide a content of hydrophilic ethylene oxide units of up to about 40% by weight, preferably about 5 to 40% by weight and more preferably about 10 to 35% by weight, based on the weight of the polyisocyanate. The compounds containing ionic groups or potential ionic groups contain at least one, preferably two, isocyanate-reactive groups and are used in an amount of up to about 120 milliequivalents, preferably about 5 to 80 milliequivalents, more preferably about 10 to 60 milliequivalents and most preferably about 15 to 50 milliequivalents per 100 grams of polyisocyanate.

Hydrophilic components having terminal or lateral hydrophilic chains containing ethylene oxide units include compounds corresponding to the formulae

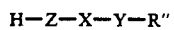

or

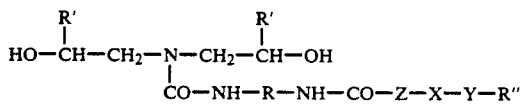

wherein

R represents a difunctional radical obtained by removing the isocyanate groups from a diisocyanate corresponding to those previously set forth, R' represents hydrogen or a monovalent hydrocarbon radical containing from 1 to 8 carbon atoms, preferably hydrogen or a methyl group, R" represents a monovalent hydrocarbon radical having from 1 to 12 carbon atoms, preferably an unsubstituted alkyl radical having from 1 to 4 carbon atoms, X represents the radical obtained by removing the terminal oxygen atom from a polyalkylene oxide chain having from 5 to 90 chain members, preferably 20 to 70 chain members, wherein at least about 40%, preferably at least about 65%, of the chain members comprise ethylene oxide units and the remainder comprises other alkylene oxide units such as propylene oxide, butylene oxide or styrene oxide units, preferably propylene oxide units, Y represents oxygen or —NR'"— wherein R'" has the same definition as R" and Z represents a radical which corresponds to Y, but may additionally represent —NH—.

The compounds corresponding to the above formulae may be produced by the methods according to U.S. Pat. Nos. 3,905,929, 3,920,598 and 4,190,566 (the disclosures of which are herein incorporated by reference). The monofunctional hydrophilic synthesis components are produced, for example, by alkoxylating a monofunctional compound such as n-butanol or N-methyl butylamine, using ethylene oxide and optionally another alkylene oxide, preferably propylene oxide. The resulting product may optionally be further modified (although this is less preferred) by reaction with ammonia to form the corresponding primary amino polyethers.

The compounds containing ionic groups or potential ionic groups for providing hydrophilicity to the polyisocyanates may be cationic or anionic. Examples of anionic groups include carboxylate groups and sulphonate groups. Examples of cationic groups include tertiary and quaternary ammonium groups and tertiary sulphonium groups. The ionic groups are formed by neutralizing the corresponding potential ionic groups either prior to, during or after their reaction with the polyisocyanate. When the potential ionic groups are neutralized prior to forming the modified polyisocyanate, ionic groups are incorporated directly. When neutralization is performed subsequent to forming the prepolymer, potential ionic groups are incorporated. Suitable compounds for incorporating the previously discussed carboxylate, sulphonate, tertiary sulphonium and tertiary or quaternary ammonium groups are described in U.S. Pat. Nos. 3,479,310, 4,108,814, 3,419,533 and 3,412,054, the disclosures of which are herein incorporated by reference.

In addition to the previously discussed hydrophilic modifiers, which are chemically incorporated into the polyisocyanates, it is also possible to use external emulsifiers which may be anionic, cationic or nonionic. Further, when dispersion stability is not a specific requirement, it is possible to disperse the polyisocyanate in water in the absence of emulsifiers by using high shear mixers, for example, those disclosed in British Patents 1,414,930, 1,432,112 and 1,428,907 as well as German Offenlegungsschrift 2,347,299. Low shear mixers may also be used to disperse the polyisocyanates in water such as the stator-rotor dynamic mixer disclosed in U.S. Pat. No. 4,742,095.

The polyisocyanates to be dispersed in water preferably have a functionality of at least 2, more preferably at least 2.2. These compounds may be prepared by reacting polyisocyanates having functionalities of greater than 2 with a monofunctional compound containing hydrophilic groups, provided that the average functionality remains at least 2. When diisocyanates are used as the polyisocyanate, it is preferred to use difunctional compounds containing hydrophilic groups in order to maintain a functionality of at least 2. The treatment of diisocyanates with monofunctional compounds containing hydrophilic groups is less preferred since this reduces the functionality to less than 2. Accordingly, the functionality of the component containing hydrophilic groups and the functionality of the polyisocyanate must be taken into consideration in order to ensure that the modified polyisocyanates have functionalities of at least 2.

The polyisocyanate dispersions generally have a solids content of about 2 to 50, preferably about 10 to 30 weight percent.

After the polyisocyanates have been dispersed in water, at least a portion of the isocyanate groups of the polyisocyanates are reacted with a monofunctional blocking agent which is more reactive with isocyanate groups than water. Examples of suitable blocking agents include secondary aromatic amines such as N-methylaniline; the N-methyl toluidines, N-phenyl toluidine and N-phenyl xylidene; N-alkyl amides such as N-methyl acetamide; imides such as succinimide; lactams such as ε-caprolactam and δ-valerolactam; mercaptans such as methylmercaptan, ethyl mercaptan, butyl mercaptan, 2-mercapto-benzothiazole and dodecyl mercaptan; triazoles such as 1H-1,2,4-triazole; preferably alkali metal bisulfites; and more preferably oximes.

The oximes preferably correspond to the formula $$HO-N=C(R_1)(R_2)$$

wherein $R_1$ and $R_2$ may be the same or different and represent hydrogen or an alkyl or aralkyl group having 1 to 10 carbon atoms, provided that both $R_1$ and $R_2$ are not hydrogen, or the two groups together with the oxime carbon atom may form a cycloaliphatic ring containing 4 to 8 carbon atoms.

Suitable oxime blocking agents include methyl ethyl ketoxime, methyl isobutyl ketoxime, acetone oxime, cyclohexanone oxime and methyl n-amyl ketoxime, methyl n-propyl ketoxime, methyl isopropyl ketoxime, diethyl ketoxime, methyl sec-butyl ketoxime, ethyl butyl ketoxime and acetophenone oxime.

The equivalent ratio of monofunctional blocking groups to isocyanate groups is 0.5:1 to 2:1, preferably about 0.8:1 to 1.2:1, more preferably 0.9:1 to 1.1:1 and most preferably about 1:1. If an excess of the blocking agent is used, the excess may be removed after the blocking reaction is complete. However, to avoid the necessity of removing excess blocking agent, it is preferred not to use an excess of the blocking agent.

Any isocyanate groups which are not blocked by the blocking agent may be left to react with water. In accordance with another, less preferred embodiment of the present invention, a portion of the isocyanate groups of the dispersed polyisocyanate may also be reacted with isocyanate-reactive compounds which are more reactive with isocyanate groups than water and have a functionality of at least 2. Examples of these compounds are the polyamines having a molecular weight of less than 400 and containing two or more primary and/or secondary amino groups which are disclosed in copending application, U.S. Ser. No. 07/677,010, filed Mar. 28, 1991, now U.S. Pat. No. 5,191,012, the disclosure of which is herein incorporated by reference.

The amount of the these isocyanate-reactive compounds is chosen to provide an equivalent ratio of isocyanate-reactive groups which are more reactive than water to isocyanate groups of the dispersed polyisocyanate of less than 0.4:1.0, preferably less than 0.2:1.0 and more preferably less than 0.1:1.0. Lower limits for the amount of these compounds are chosen to provide an equivalent ratio of isocyanate-reactive groups which are more reactive than water to isocyanate groups of 0.02:1.0, preferably 0.05:1.0.

It is believed that the amino groups react with the isocyanate groups on the surface of the dispersed polyisocyanates to form urea groups which encapsulate the dispersed polyisocyanates. Because this encapsulation may interfere with the reaction between the isocyanate groups and the blocking agent, it is preferred not to add significant amounts of the polyamines for reaction with the dispersed polyisocyanate. If the incorporation of urea groups is desired, it is possible to react the polyamines with the polyisocyanate before the polyisocyanate is dispersed in water as previously described.

The blocking agent and optional isocyanate-reactive compound may be added to the water either before, during or after the polyisocyanate has been dispersed. Preferably, the polyisocyanate is first dispersed in water and then the blocking agent and optional isocyanate-reactive compound are added to the dispersed polyisocyanate. In one embodiment of the present invention the polyisocyanate may be dispersed in water in a first mixing step, and subsequently the blocking agent can be added to this mixture in a second mixing step. Suitable apparatus for performing these mixing steps have previously been disclosed for dispersing the polyisocyanate in water and also include the mixing apparatus disclosed in copending application, U.S. Ser. No. 07/677,002, filed Mar. 28, 1991, now U.S. Pat. No. 5,221,710, the disclosure of which is herein incorporated by reference.

In accordance with the present invention, it is also possible to incorporate additives into the aqueous dispersions of encapsulated polyisocyanates. The additives may be present in the form of a solution or in the form of an emulsion or dispersion. These additives are known and include catalysts such as tertiary amines, aminosilanes having carbon-silicon bonds, ammonium hydroxides and organo metallic compounds; surface-active agents; reaction retarders; and adhesion promoters. Examples of suitable additives which may optionally be used in accordance with the present invention and details on the way in which these additives are to be used and how they function may be found in Kunststoff-Handbuch, Vol. VII, published by Vieweg and Hochtlen, Carl-Hanser-Verlag, Munich 1966, for example on pages 103 to 113.

The aqueous dispersions of blocked polyisocyanates prepared in accordance with the present invention may be used alone, e.g., as binders for fiberglass, or they may be used as crosslinkers for aqueously dispersed polyurethanes which may optionally contain hydroxyl and/or amino groups. The dispersions according to the present invention are also suitable to improve the properties (such as adhesion, solvent resistance and abrasion resistance) of many other aqueous polymer dispersions such as acrylic, epoxy, polyvinyl acetate and styrene/butadiene rubber dispersions.

Another feature of the aqueous dispersions of blocked polyisocyanates is that after the blocking reaction is complete, water soluble or dispersible isocyanate co-reactants can be added. These co-reactants can react with the polyisocyanates under the influence of heat after evaporation of the water and release of the blocking agent. Suitable co-reactants include compounds which have a molecular weight (as determined by end group analysis) of 32 to 10,000; contain two or more isocyanate-reactive groups, preferably hydroxyl and/or amino groups; and are either water soluble or dispersible in water, optionally in the presence of an external emulsifier. Preferably, these compounds do not contain urethane groups.

Examples of these compounds include the known low molecular weight chain extenders having a molecular weight of 32 to less than 400 such as polyols and polyamines. Also suitable are the known polyhydroxyl and polyamino polyesters, polylactones, polycarbonates, polyethers, polythioethers, polyacetals, polyether esters, polyester amides and polyamides having a molecular weight of 400 to 10,000, preferably 1000 to 6000. Examples of all of these compounds are disclosed in U.S. Pat. No. 4,925,885, the disclosure of which is herein incorporated by reference.

The invention is further illustrated but is not intended to be limited by the following examples in which all parts and percentages are by weight unless otherwise specified.

EXAMPLES

Example 1

Preparation of Aromatic Water-Dispersible Polyisocyanate

A three liter round bottom flask equipped with a thermometer, drying tube, condenser, and stirrer was charged with 1366 grams of Crude MDI[1] and 683 grams of a monofunctional poly(ethylene oxide) ether[2]. The temperature of the reaction flask was increased to 80° C. The reaction proceeded at this temperature for four hours at which time the isocyanate content was determined by titration to be 20.48% (theoretical NCO=20.68%). The prepolymer was cooled to ambient temperature and placed in dry bottles for later use.

1. An aniline/formaldehyde condensation product containing 4,4'-diphenylmethane diisocyanate and about 50% of higher functionality homologs and having an isocyanate content of about 31.5% and a viscosity at 25° C. of 200 mPa.s.

2. A polyether monohydric alcohol having a molecular weight of 2200 and prepared from n-butanol, ethylene oxide and propylene oxide (molar ratio of ethylene oxide to propylene oxide—83:17).

Example 2

Preparation of Aliphatic Water-Dispersible Polyisocyanate

A one liter round bottom flask equipped with a thermometer, drying tube, condenser, and stirrer was charged with 400 grams of the isocyanurate of hexamethylene diisocyanate (isocyanate content 21.25%) and 200 grams of the monofunctional poly(ethylene oxide) ether described in Example 1. The temperature of the reaction flask was increased to 90° C. The reaction proceeded at this temperature for five hours at which time the isocyanate content was determined by titration to be 13.22% (theoretical NCO=13.54%). The viscosity of the prepolymer was 3300 mPa.s @ 25° C. The modified polyisocyanate was cooled to ambient temperature and placed in dry bottles for later use.

Example 3

Preparation of an Aqueous Blocked Aromatic Polyisocyanate 22.1 grams of methyl ethyl ketoxime were added to a two liter resin flask containing 649 grams of demineralized water. This mixture was agitated at ambient temperature while 50 grams of the water-dispersible polyisocyanate of Example 1 were added over a two minute period. This corresponded to an equivalent ratio of oxime groups to isocyanate groups of 1.0:1.0. The resulting stable dispersion had a low viscosity of <50 mPa.s at 25° C. and an isocyanate content of 0.20% after 15 minutes. After 50 minutes the isocyanate content was 0.14%. This corresponded to the reaction of about 90% of the available isocyanate groups with the blocking agent.

Example 4

Preparation of an Aqueous Blocked Aliphatic Polyisocyanate 300 grams of the water-dispersible polyisocyanate of Example 2 were added to a two liter resin flask containing 475 grams of demineralized water at ambient temperature and under agitation. Immediately following the dispersing of the polyisocyanate, 82 grams of methyl ethyl ketoxime was added to the flask. This corresponded to an equivalent ratio of oxime groups to isocyanate groups of 1.0:1.0. The reaction mixture exothermed to 43° C. The temperature was maintained at 35°-40° C. for an additional four hours at which time the dispersion was isocyanate free. The aqueous blocked polyisocyanate had a viscosity of 430 mPa.s @ 25° C. and a pH of 7.35.

Example 5

Preparation of an Aqueous Blocked Aromatic Polyisocyanate 200 grams of the water-dispersible polyisocyanate of Example 1 were dispersed in a two liter resin flask containing 246 grams of demineralized water at ambient temperature and under agitation. Immediately following the dispersing of the polyisocyanate, 125 grams of methyl n-amyl ketoxime were added to the flask. This corresponded to an equivalent ratio of oxime groups to isocyanate groups of 1.0:1.0. The reaction mixture exothermed to 50° C. After approximately nine minutes no isocyanate was detectable in the dispersion. The aqueous blocked polyisocyanate at 35% solids had a viscosity of 9000 mPa.s @ 25° C. and a pH of 4.4.

Example 6

Preparation of an Aqueous Blocked Aromatic Polyisocyanate 200 grams of the water-dispersible polyisocyanate of Example 1 were dispersed in a two liter resin flask containing 246 grams of demineralized water at ambient temperature and under agitation. Immediately following the dispersing of the polyisocyanate, 112 grams of methyl isobutyl ketoxime were added to the flask. This corresponded to an equivalent ratio of oxime groups to isocyanate groups of 1.0:1.0. The reaction mixture exothermed to 53° C. After approximately nine minutes no isocyanate was detectable in the dispersion. The aqueous blocked polyisocyanate at 35% solids had a viscosity of 2700 mPa.s @ 25° C. and a pH of 4.2.

Example 7

Preparation of a Partially Blocked Aqueous Aromatic Polyisocyanate 200 grams of the water-dispersible polyisocyanate of Example 1 were dispersed in a two liter resin flask containing 246 grams of demineralized water at ambient temperature and under agitation. Immediately following the dispersing of the polyisocyanate, 63 grams of methyl ethyl ketoxime were added to the flask. This corresponded to an equivalent ratio of oxime groups to isocyanate groups of 0.75:1.0. The reaction mixture exothermed to 47° C. After approximately one minute the isocyanate content of the dispersion was 1.41%. This corresponded to blocking of 75% of the isocyanate as well as a minor amount of isocyanate reaction with the water. In the next 80 minutes the isocyanate content dropped to 0.62% which corresponded to 91% reaction of the isocyanate (including blocking). At this time the aqueous blocked polyisocyanate at 35% solids had a viscosity of 380 mPa.s @ 25° C. and a pH of 3.

Comparative Example 1

Preparation of an Aqueous Blocked Aromatic Polyisocyanate

To a glass vessel were charged 125 grams of the polyisocyanate from Example 1 and 53 grams of methyl ethyl ketoxime. This corresponded to an equivalent ratio of oxime groups to isocyanate groups of 1.0:1.0. The mixture was agitated and allowed to exotherm freely to 98° C. After 5 minutes, the isocyanate content was determined by titration to be 0.44%. This corresponded to a reaction of 97% of the isocyanate groups with the blocking agent.

The sample was placed in a 60° C. oven for an additional two hours. The viscosity at that time was 200,000 mPa.s @ 60° C. The material was allowed to cool overnight. The following morning the blocked polyisocyanate was a solid at room temperature and no isocyanate could be detected. The solid could not be dispersed in water at room temperature. The viscosity of the blocked polyisocyanate was reduced to about 25,000 mPa.s by heating to 80° C. At this temperature it could be successfully dispersed into water held at 70° C. The dispersion had a viscosity of 80 mPa.s at 25° C. and a pH of 4.1.

Comparative Example 2

Preparation of an Aqueous Blocked Aliphatic Polyisocyanate

To a glass vessel were charged 150 grams of the polyisocyanate from Example 2 and 41 grams of methyl ethyl ketoxime. This corresponded to an equivalent ratio of oxime groups to isocyanate groups of 1.0:1.0. The mixture was agitated and allowed to exotherm freely to 80° C. After 15 minutes, the isocyanate content was determined by titration to be 0.33%. This corresponds to a reaction of 97% of the isocyanate groups with the blocking agent.

The sample was placed in a 60° C. oven for an additional one and a half hours. The viscosity at that time was 5000 mPa.s @ 60° C. The material was allowed to cool overnight. The following morning the blocked polyisocyanate had a viscosity of 180,000 mPa.s @ 25° C. and a small amount of residual isocyanate could be detected. The material was too viscous to be successfully dispersed into water at room temperature. The viscosity of the blocked polyisocyanate was reduced to about 1700 mPa.s by heating to 78° C. At 65° C. it could be successfully dispersed into water held at 60° C. The dispersion had viscosity of 100 mPa.s at 25° C. and a pH of 6.7.

Although the invention has been described in detail in the foregoing for the purpose of illustration, it was to be understood that such detail was solely for that purpose and that variations can be made therein by those skilled in the art without departing from the spirit and scope of the invention except as it may be limited by the claims.

What is claimed is:

1. A process for the preparation of an aqueous dispersion of a blocked polyisocyanate which comprises reacting an aqueously dispersed polyisocyanate having an isocyanate content of at least 12% by weight, based on the weight of the polyisocyanate, with a monofunctional blocking agent which is more reactive with isocyanate groups than water at an equivalent ratio of monofunctional blocking groups to isocyanate groups of 0.5:1 to 2:1, wherein said monofunctional blocking agent comprises a member selected from the group consisting of secondary aromatic amines, N-methyl toluidines, alkyl amides, imides, lactams, mercaptans, triazoles, alkali metal bisulfites and oximes.

2. The process of claim 1 wherein said monofunctional blocking agent comprises an oxime which corresponds to the formula $$HO-N=C(R_1)(R_2)$$

wherein
$R_1$ and $R_2$ may be the same or different and represent hydrogen or an alkyl or aralkyl group having 1 to 10 carbon atoms, provided that both $R_1$ and $R_2$ are not hydrogen, or the two groups together with the oxime carbon atom may form a cycloaliphatic ring containing 4 to 8 carbon atoms.

3. The process of claim 1 which comprises rendering the polyisocyanate hydrophilic by reacting the polyisocyanate with a compound containing a lateral or terminal nonionic hydrophilic group prior to dispersing the polyisocyanate in water.

4. The process of claim 1 wherein said equivalent ratio of monofunctional blocking groups to isocyanate groups is 0.8:1.0 to 1.2:1.0.

5. The process of claim 2 wherein said equivalent ratio of monofunctional blocking groups to isocyanate groups is 0.8:1.0 to 1.2:1.0.

6. The process of claim 3 wherein said equivalent ratio of monofunctional blocking groups to isocyanate groups is 0.8:1.0 to 1.2:1.0.

7. The process of claim 2 which comprises rendering the polyisocyanate hydrophilic by reacting the polyisocyanate with a compound containing a lateral or terminal nonionic hydrophilic group prior to dispersing the polyisocyanate in water.

8. The process of claim 7 wherein said equivalent ratio of monofunctional blocking groups to isocyanate groups is 0.8:1.0 to 1.2:1.0.

* * * * *